(12) United States Patent
Lolachi et al.

(10) Patent No.: US 7,070,589 B2
(45) Date of Patent: Jul. 4, 2006

(54) STERILITY-MAINTAINING CONNECTION SYSTEM FOR MEDICAL SYSTEMS AND USE THEREOF

(75) Inventors: Houshang Lolachi, Rockville, MD (US); Hans-Jürgen Neumann, St. Wendel (DE); Siegfried Ebner, St. Wendel (DE)

(73) Assignee: Fresenius AG, Bad Homburg (DE)

( * ) Notice: Subject to any disclaimer, the term of this patent is extended or adjusted under 35 U.S.C. 154(b) by 670 days.

(21) Appl. No.: 09/729,924

(22) Filed: Dec. 6, 2000

(65) Prior Publication Data

US 2002/0133136 A9    Sep. 19, 2002

(30) Foreign Application Priority Data

Dec. 14, 1999  (DE) ................. 199 60 226

(51) Int. Cl.
*A61M 25/18* (2006.01)
(52) U.S. Cl. ..................... 604/537; 141/346
(58) Field of Classification Search ............. 604/537, 604/533, 411, 413; 141/383, 346; 222/83, 222/83.5; 206/1.5; 239/271, 272, 309; 285/3, 285/4, 914, 328
See application file for complete search history.

(56) References Cited

U.S. PATENT DOCUMENTS

| | | | |
|---|---|---|---|
| 3,749,271 A | 7/1973 | Ellis, Jr. et al. | 215/32 |
| 4,007,738 A | 2/1977 | Yoshino | 128/214 D |
| 4,265,280 A * | 5/1981 | Ammann et al. | 141/98 |
| 5,270,003 A | 12/1993 | Bernes et al. | 422/44 |
| 5,743,892 A | 4/1998 | Loh et al. | 604/283 |
| 5,792,120 A | 8/1998 | Menyhay | 604/256 |
| 6,170,529 B1 | 1/2001 | Howe | 138/89 |

FOREIGN PATENT DOCUMENTS

| | | |
|---|---|---|
| DE | 296 07 437 | 10/1997 |
| EP | 0 555 927 | 8/1993 |
| WO | 81/01105 | 4/1981 |
| WO | 94/12224 | 6/1994 |

* cited by examiner

*Primary Examiner*—Henry Bennett
*Assistant Examiner*—Camtu Nguyen
(74) *Attorney, Agent, or Firm*—Jacobson Holman PLLC

(57) ABSTRACT

A connection system including at least a male connecting element and a female connecting element which can be connected to each other, as well as the male connecting element and the female connecting element. The location of contact of the two connecting elements is preferably provided with a disinfecting adhesive so that an aseptic or sterile connection can be established. Therein both connecting elements have predetermined breaking points which in the connected state are arranged one above the other so that only one breaking point within the tube is obtained via which an aseptic fluid guidance through two tubes from one sterile system to another sterile system can be carried out. Thereby a particularly simple and cost-saving connection is created which fulfills the highest sterility requirements. Furthermore, also the use of such a connection system is described.

21 Claims, 11 Drawing Sheets

Fig.6
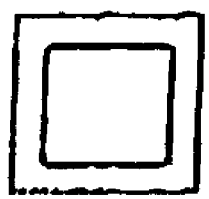
(c)
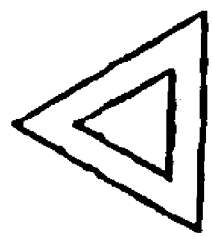
(b)
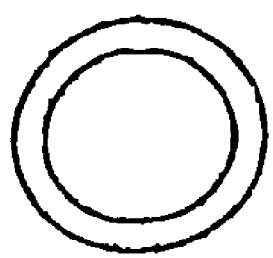 
(a)            (a)

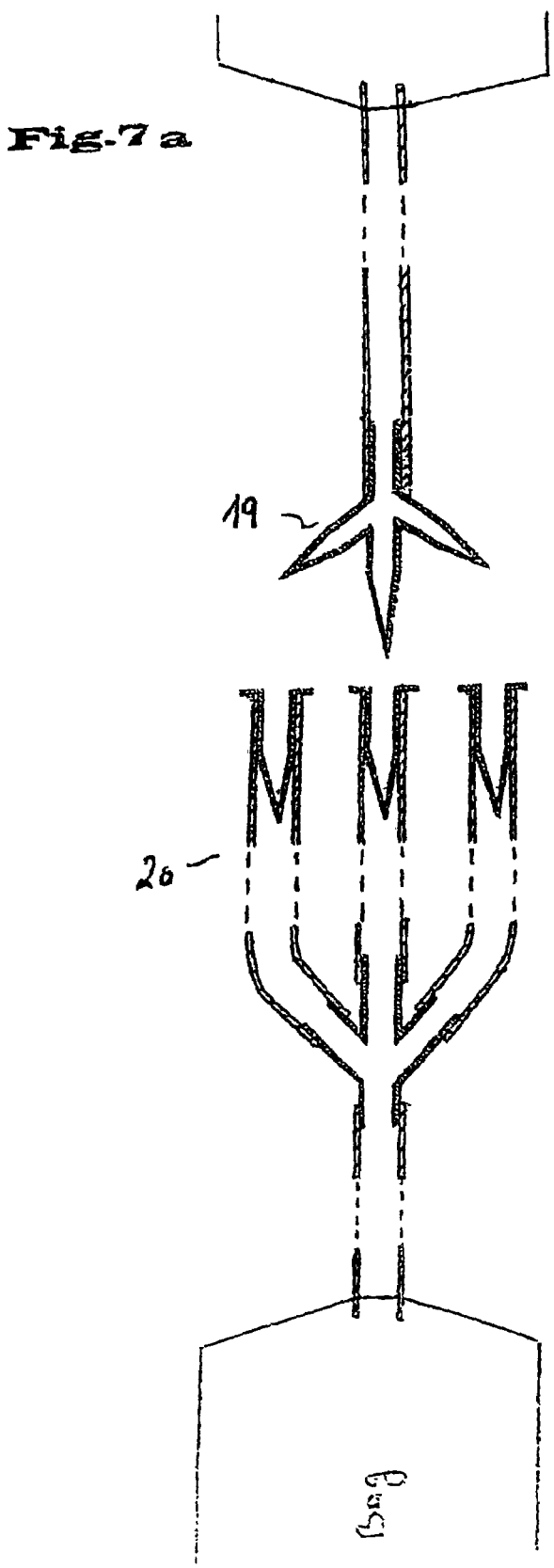

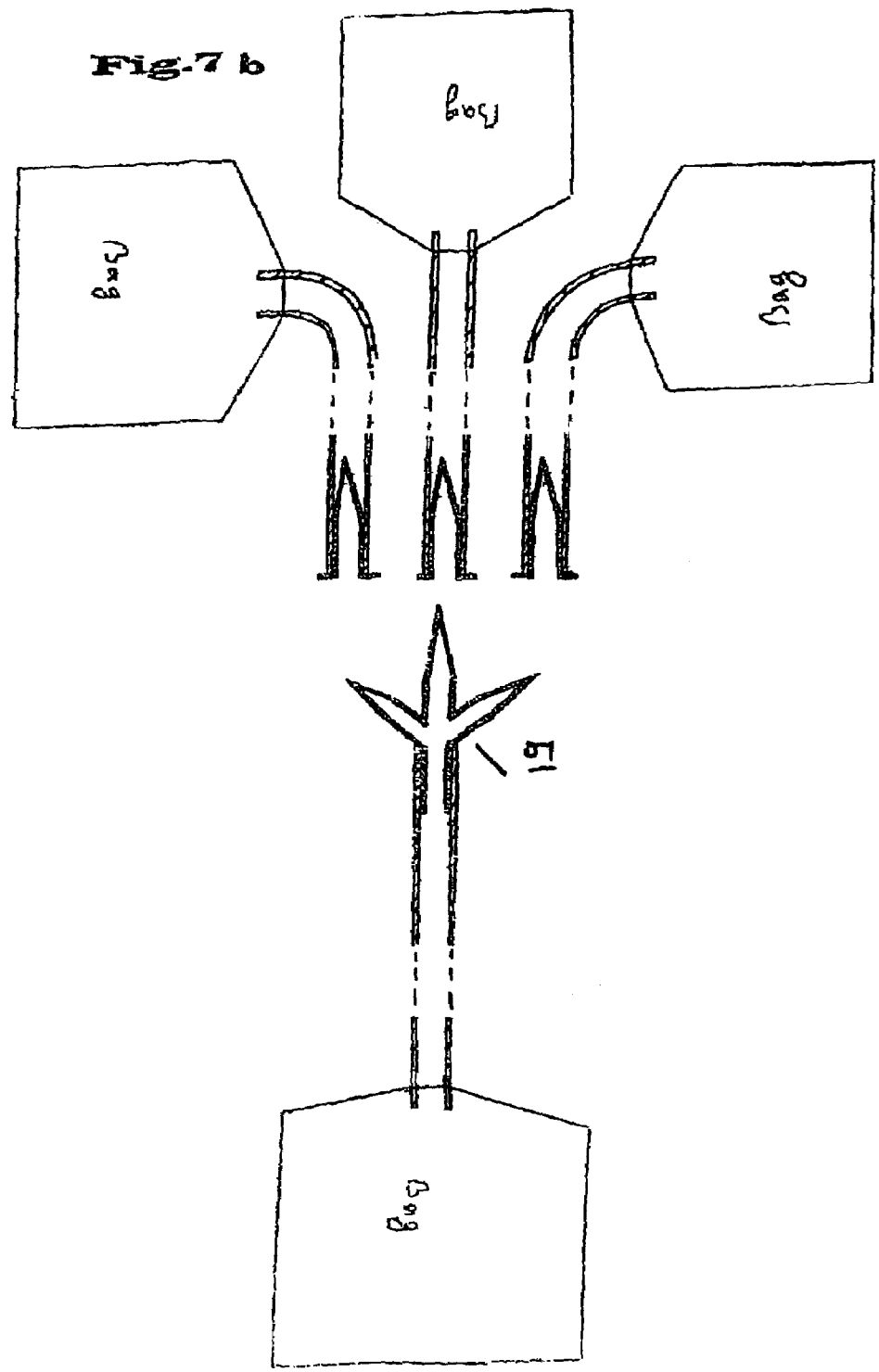

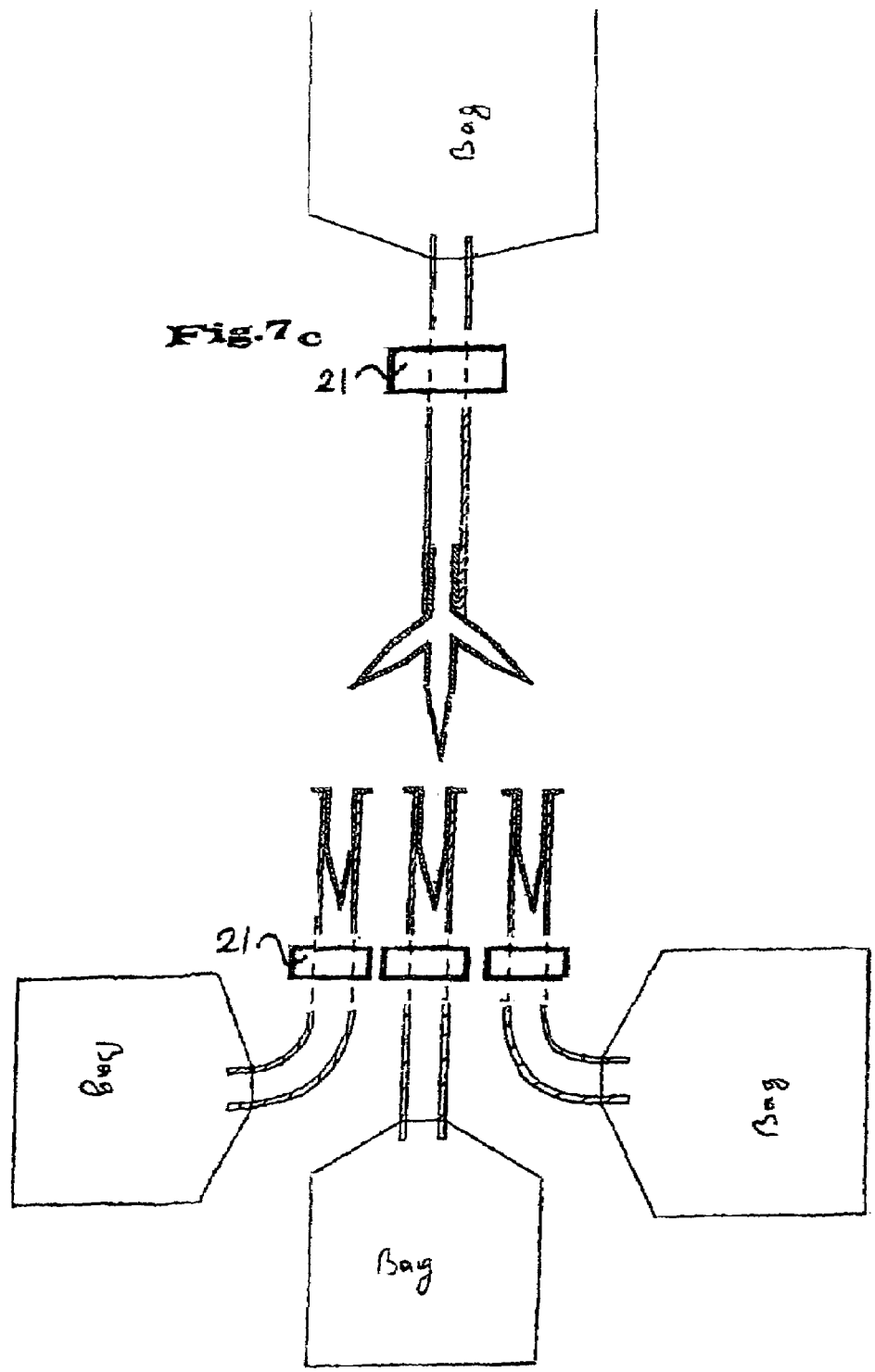

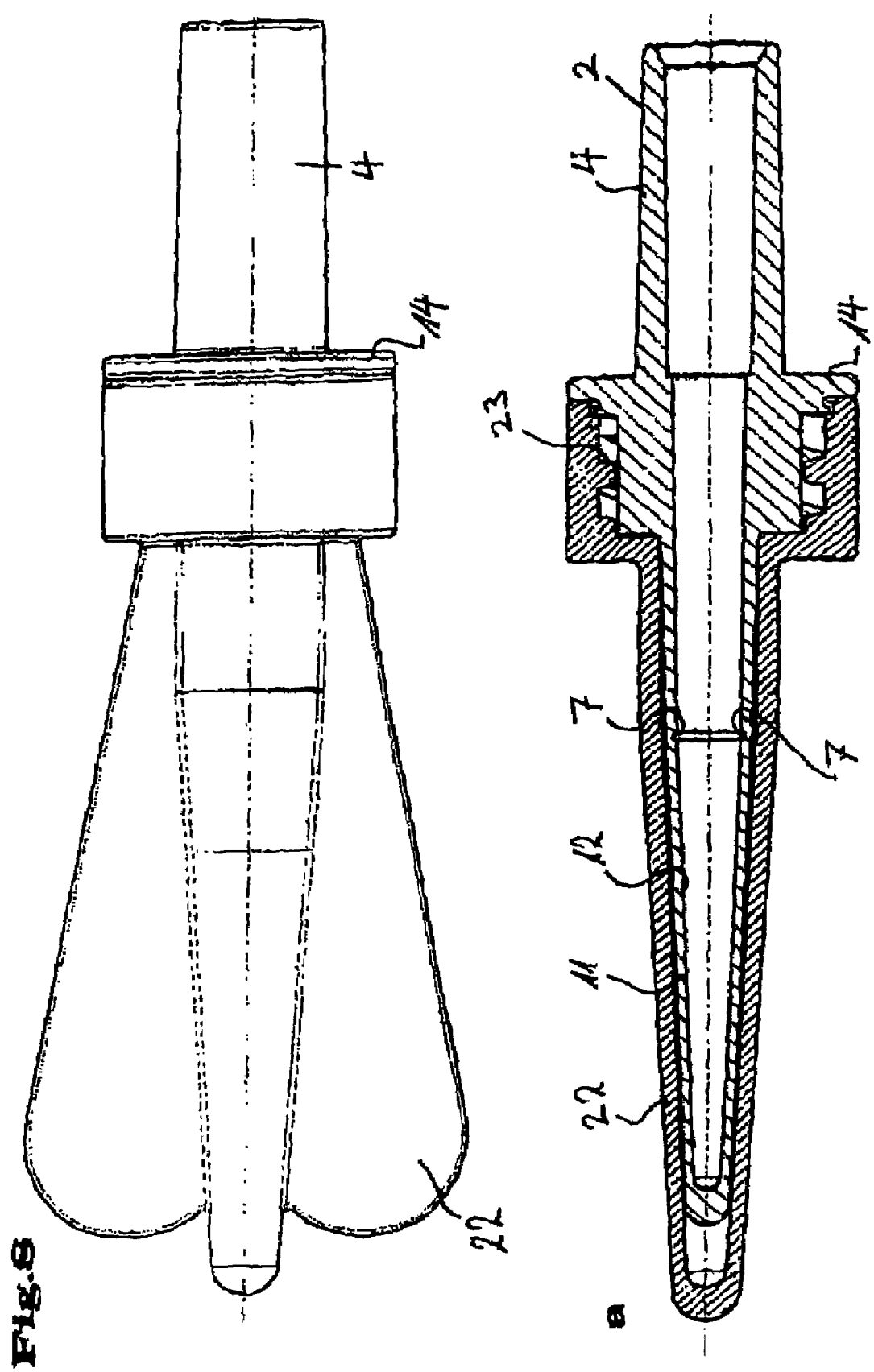

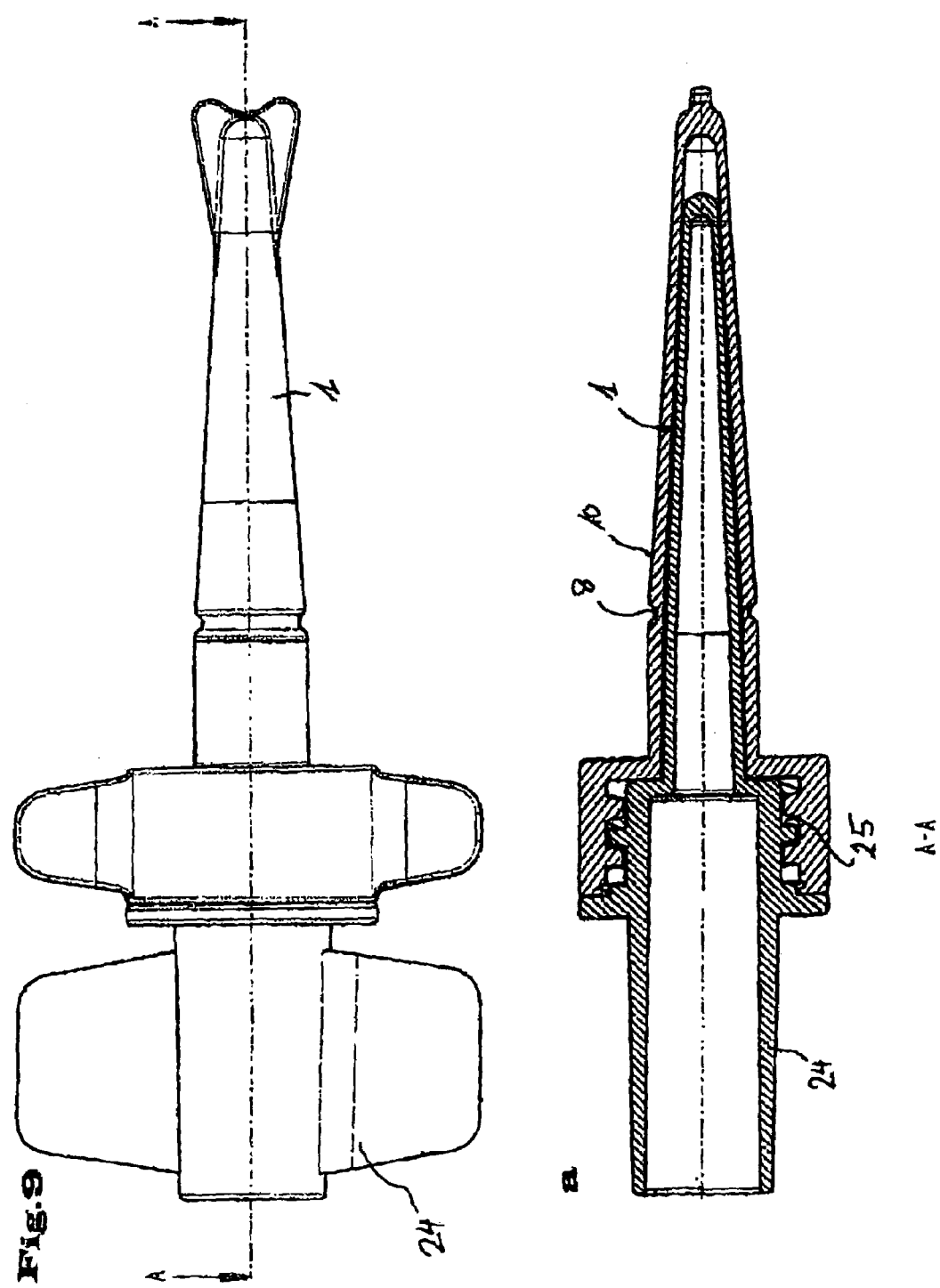

STERILITY-MAINTAINING CONNECTION SYSTEM FOR MEDICAL SYSTEMS AND USE THEREOF

BACKGROUND OF THE INVENTION

1. Field of the Invention

The invention relates to a sterile and/or aseptic connection system and the use thereof in medical systems, especially in a set for cell separation for the sterile connection of further bags to an existing set. The invention relates in particular to two connecting elements which are connectable to each other in a sterile and/or aseptic manner, for transporting a fluid from one closed sterile bag into a second sterile bag.

2. Description of the Related Art

In prior art there are known numerous connectors which, in part, also enable a sterile connection. Said connection systems have become necessary in order to avoid any contaminations during the transfer of liquids which have to be kept sterile. This is for instance required for the transfer of infusion solutions, dialysis solutions or blood or blood components. In the field of infusion technology, several transfer systems are known which usually consist of a septum and the pertinent needle. When transferring liquids for the enteral feeding, spikes are used which have a larger flow volume.

While the sterility of the spikes and cannulas in the infusion, i.e. the direct use of the solutions, usually is sufficient, an increased sterility requirement has to be fulfilled regarding the sterility of blood or blood components to be stored or regarding the transfer a dialysis into the peritoneum in order to avoid a microbic contamination. Such solutions, on the one hand, provide an optimum culture medium for bacteria and a and, con the other hand, in most cases they also provide an optimum temperature environment. In case of a peritoneal solution, a germ could cause a peritonitis, i.e. an inflammation of the peritoneum, which can lead to irreparable damage. In the case of products to be stored, by ideal reproduction conditions the number of germs increases such that the immunological system is overstrained with a corresponding defense or resistance.

Therefore it is demanded and usual that for the transfer of blood from one closed system to a second system as well as for the transfer of solutions into the peritoneal cavity a sterile connection is used which provably cannot be contacted at its point of connection by the medical staff or by the patient himself or herself, not even inadvertently.

Therefore, in known sterile connectors the closing element itself, for instance the screw cap, is displaced inwardly and is protected against contact by a wrapping element drawn over the cap.

Contamination is also possible by air contact so that connection systems are also known which have an internal disinfecting means—for instance soaked little sponges—so that when the elements are assembled, a disinfectant like iodine PVP is set free and thereby a microbic contamination is prevented. But in such systems a part of the disinfectant passes into the tube connection. In view of this it has to be guaranteed that the disinfectant does not cause any damage or harm.

Furthermore it is known to establish the fluid connection only when the connection system has already been closed in a sterile manner. In WO 81/01105 there is shown a predetermined breaking point inside a tube which renders possible the flowing-through by breaking off the plastic pin. Said system, however, is produced with a fixed tube coupling and is sterilized thereafter, so that no connection is required.

In DE 29607437 U there is for instance described a medicotechnical connecting device with an internal threat th,e fluid connection of which is enabled by opening a break seal located in an inner cone axially spaced apart from the insertion end and therefore can only be penetrated by the outer cone of the counter connector.

A particularly quick and safe opening of the fluid path is realized by breaking off, as is for instance described in EP 0 555 927 A2. In said publication a connecting element is described which sealingly closes the end of a tube. A predetermined breaking line enables the breaking-off of the seal at the accurate position in order to open the outlet.

Also in WO 94/12224 there is shown a blood tube system which shows a clamp with a predetermined breaking point on a supply tube. By means of said clamp the tube can be alternatively only clamped off from the inlet section or it can be separated by breaking off at the predetermined breaking point, It is already known from U.S. Pat. No 4,007,738 to provide an in-lying predetermined breaking point for a connecting element, with an end part of a connecting tube being broken off at a predetermined breaking point located within a small connecting tube This broken-off part can, however, result in an unwanted plugging of the line in the solution proposed there.

A connection system is known from U.S. Pat. No. 5,743,892 where a reservoir with disinfectant means is already provided which serves to disinfect the connection point when the female and male connecting elements are put together.

It is an object of the present invention to develop a connection system which satisfies high sterility requirements, but can nevertheless be produced in a simple and cost-saving manner. Said object is solved by the features mentioned in claim 1.

SUMMARY OF THE INVENTION

It is an object of the present invention to develop a connection system which satisfies high sterility requirements, but can nevertheless be produced in a simple and cost-saving manner. This object is solved by the present invention which is directed to a connection system for the connection of, in particular, two or more sterile systems. The connection system includes at least one male connecting element forming a closed end of a sterile, fluid-containing system and at least one female connecting element forming the closed end of a second sterile, fluid-containing system which can be aseptically connected to one another. Both of the connecting elements each have a predetermined breaking point, with the breaking points being arranged one above the other when the two connecting elements are assembled so that they form a common predetermined breaking point and can be broken off together, with the predetermined breaking point being located inside the fluid-containing system.

The connection is to be made for instance by a screw thread or via snap-in element. Preferably the two connecting elements, however, are joined with each other by means of an adhesive, in a preferred embodiment, the connecting element are irreversibly joined to one another in order to achieve additional security.

A marking, e.g. a stop or a catch, at the connecting elements allows to determine whether a positive locking of the connection has been obtained or not.

Therein both parts each have a predetermined breaking point which, after the positive connection, lie as close to each other as possible. Even when tolerances are possible, the predetermined breaking points should preferably be arranged directly one above the other. Said position guarantees that when the predetermined breaking points are broken a common breaking position is obtained at which the fluid to be transferred can exit.

The contact portion of the connection system is provided with an adhesive which has a disinfecting effect. Thereby a thread or another connection difficult to be established can be avoided For the connection by means of an adhesive there are principally two possibilities.

On the one hand, the adhesive can be disposed on the male connecting element. In this case the surface of the male connecting element is for instance dipped into a liquid adhesive or the adhesive is applied so that during the connection also a complete wetting of the point of contact is obtained. When the connector is delivered in an already wetted state, a protective covering is provided.

On the other hand, the adhesive can also be provided in the female connecting element. In this case the adhesive is preferably enclosed in a small storage container, for instance in a thin polymer cover or in a plurality of containers such as beads or microbeads within the connecting element. it is therefore possible to use a one- or multi-component adhesive encapsulated in small spheres.

When the female and male connecting elements are assembled, the adhesive reservoir will burst, and the adhesive will be uniformly spread over the entire location through the press fit. But it is also possible that the adhesive is spread over the inside and that the connector is closed in a sterile manner against the outside by means of a protective cap, a protective covering or by a glued-on pierceable protective membrane or a septum. The protective membrane can here be attached both to the female and the male connecting elements.

In a preferred embodiment, the adhesive itself has a disinfecting effect or a disinfecting means is added to the adhesive together with or in other beads. During assembly or a closing forced by snapping-in or turning, said beads or small spheres containing the adhesive and/or the disinfectant means burst and mix in order to connect the surfaces to one another and/or to disinfect.

Furthermore it is advantageous that the adhesive is quick hardening so that the connection will not be disconnected again during the use thereof. In this respect cyanoacrylate is mentioned as an example, as it has such an effect. But it is also possible that the adhesive itself is not disinfecting or that the positive locking is obtained via a thread or locking means. Then, for guaranteeing the sterility, additionally a disinfectant should be inserted between the contact surfaces of the male and the female connecting elements. When both connecting elements have been assembled, the adhesive spreads over the entire contact location and hardens or cures within a few seconds.

Then the connection is bent, whereby a break of the connected connecting elements at the predetermined breaking point is obtained, The broken-off section has to be designed such that it gets stuck in the tube but nevertheless does not form a stopper for the fluid flowing through the tube. This is obtained by the fact that the breaking point is provided not too far away at the end of the connection system, as otherwise the fragment could be too small and could be transported further on in the tube. But it may also not be provided too far away at the broad side of the connection system, as otherwise the risk of a jamming is given. Due to said reasons the predetermined breaking points are advantageously chosen such that they are provided approximately in the middle of a connection system having a long and thin structure.

As already mentioned, the predetermined breaking points of the male and female connecting elements are located one above the other in the assembled state, so that in case of a break no adhesive or disinfectant will enter the inside of the connection system. It is self-evident that tie breaking point is located inside the tube ends to be connected so that the tube itself provides the sealing against the outside.

The connector arrangement in accordance with the invention is used, for example, in bag and tube arrangements in which a connection has to be made in a sterile/aseptic way. These bag systems can be blood bag systems which often also contain a filter such as a leukocyte depletion filter. Depending on the application of these bag systems, the addition of a filter is necessary or not so that the filter, individual bags or tube pieces can be assembled freely in any way to form a complete bag systems.

It is thus naturally also possible for two or a plurality of connections to be formed at one connector system as is illustrated in the description of the figures.

Hence, by the inventive connection arrangement the contamination risk can be easily and safely avoided. This applies, on the one hand, to the medium flowing in the inside, e.g. blood, as neither adhesive or disinfectant can get into the blood, nor germs which would render the storage and the use of conserved blood impossible. And, on the other hand, by said safe and permanent glue connection also no blood can get into the environment, so that also thereby a contamination by for instances viruses cannot be transported any further.

Preferably the connecting elements are made of plastic, e.g. polycarbonate, acrylonitrile butadiene styroles, polyethylenes, polypropylenes, polystyroles, polymethyl methacrylates, polysulfones or methyl methacrylate butadiene styroles or methyl methacrylate acrylonitrile butadiene styroles which should be compatible with the tube material coming into contact with them, with the adhesive, as well as with the media flowing therethrough. In the case of blood or blood components there is suitable a PVC tube or also a polyolefine tube.

Advantageously, protective caps are provided for the male and female connecting elements, said protective caps being connectable to the respective elements and keeping these sterile and protecting them against damage until they are assembled.

BRIEF DESCRIPTION OF THE DRAWINGS

In the following a preferred embodiment of the connection system is described by way of the description of the figures.

FIG. 6 shows different forms of the connection system in intersection;

FIGS. 7 a, b and c show multi-connection systems; a/b without and c with filters;

FIGS. 8, 8*a* show a side view and a section through the male part of the connection system which is connected to a protective cap; and FIGS. 9, 9*a* show a side view and a section through the female part of the connection system to which a protective cap is connected.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
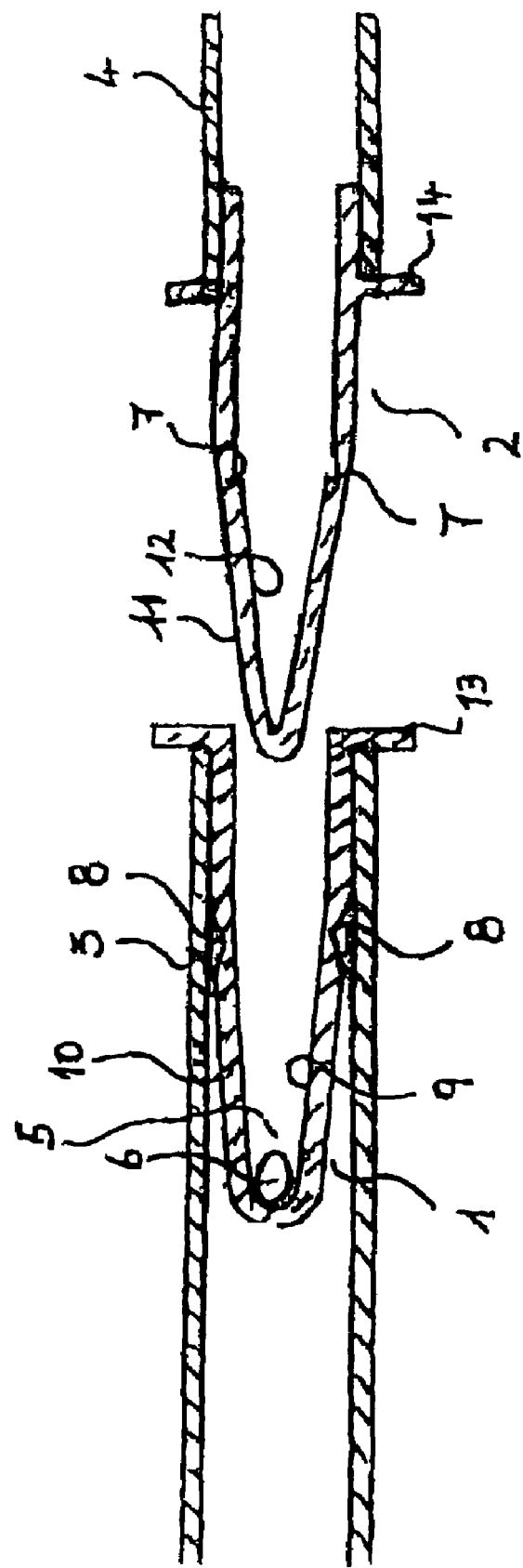
FIG. 1 shows the connection system in a disconnected state.

In FIG. 1 there is shown a connection system which serves for the connection of two tube sections 3, 4, wherein the female and the male connecting element 1, 2 are provided separately. The first tube section 3 receives one part of the female connecting element 1, so that the tip thereof comes to lie inside the tube. On the other hand, in the inner section 5 of the tip there is a storage of an aseptic adhesive 6.

The female connecting element has a predetermined breaking point 8 which results from a material saving extending circularly around the connector. In the present case the material saying is provided in the form of a circular notch at the outer section 10 so that the internal surface 9 has a smooth surface.

The male connecting element 2 is irreversibly fixed at its connection end to a tube end 4 so that the tip of the connector is freely visible. Also the male connecting element has a predetermined breaking point 7 situated, in contrast to its counterpart, in the inner section 12 so that the outer surface 11 is also smooth. The position of the predetermined breaking point is only represented in rough outlines in the present figure. As already described in the text, it has to be guaranteed that the broken end piece is wedged in the tube without preventing the flow therethrough.

Figure 2:
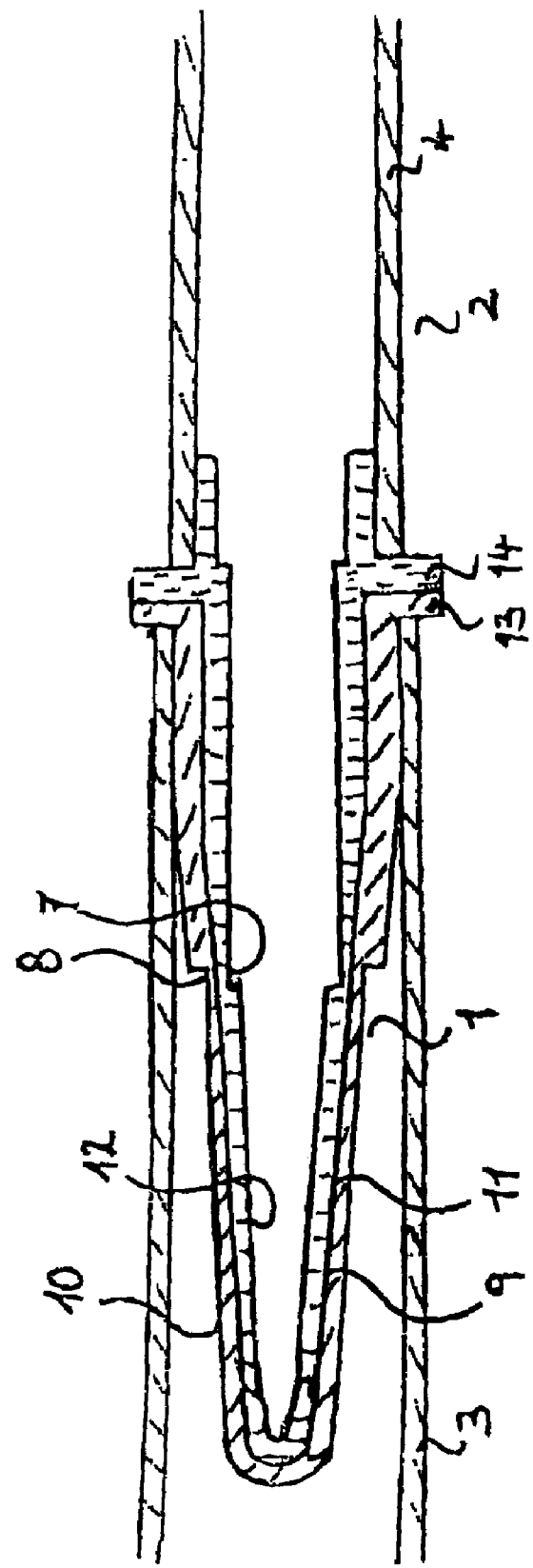
FIG. 2 shows the connection system in a connected state.

In the connected state—as shown in FIG. 2—the predetermined breaking points come to lie one above the other and thereby result in a single common predetermined breaking point. Due to the press fit, the adhesive has been uniformly spread over the surfaces 9 and 11 and positively connects the connecting elements. Advantageously, both connecting elements 1, 2 have a stop 13, 14 which indicates to the user whether the two connecting elements have been positively pressed on one another or not. In the closed state there may no longer be seen any gap between the stop 13 of the female connecting element and the stop 14 of the male connecting element. Also a canting thereof is exactly visible.

Figure 3:
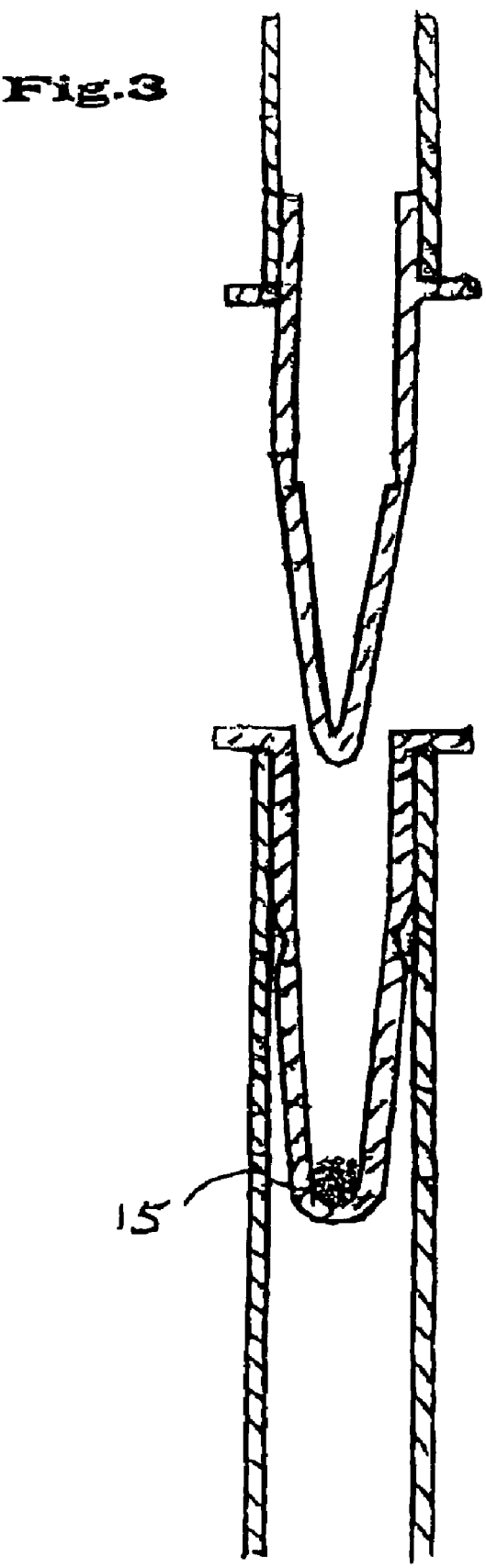
FIG. 3 shows an embodiment in which the adhesive and/or the disinfectant means is present in a plurality of micro-spheres.

FIG. 3 shows the connector system with a plurality of small beads 15 which each contain either adhesive or disinfectant means.

Figure 4:
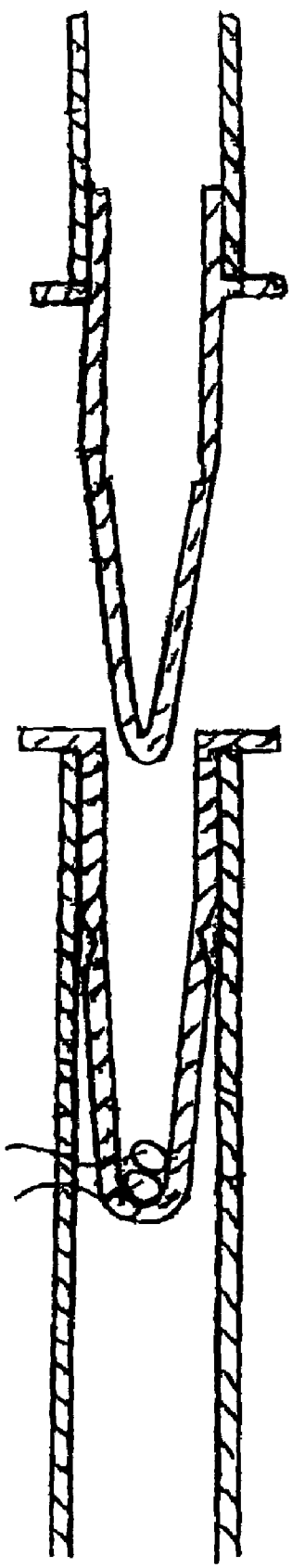
FIG. 4 shows the connection system with two beads.

FIG. 4 shows only two reservoirs 16 and 17 which should each contain one component of a two-component adhesive. The embodiments are, however, naturally not restricted to two components.

Figure 5:
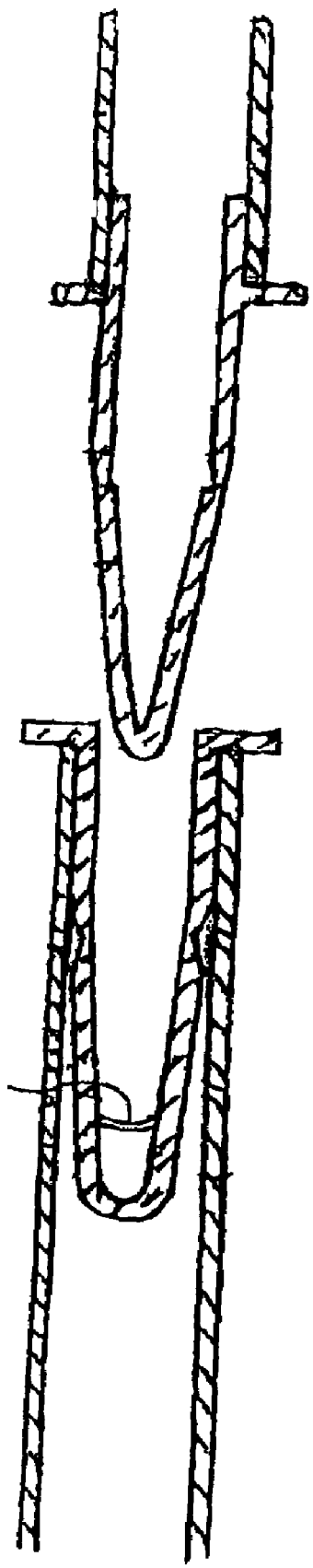
FIG. 5 shows a membrane inside the connection system as a termination.

FIG. 5 discloses a membrane 18 or a septum inside the female connection system which can be penetrated with the aid of the male part and thereby the enclosed means released FIG. 6 shows the geometric designs of the connection system with a) being circular, b) triangular, c) quadrangular and d) elliptic.

FIGS. 7 each show the multi-connections in schematic form. FIG. 7*a* shows a multi-connector 18 at the male part and at a female part 20, whereas in 7*b* the multi-connector 19 is associated with individual other female counterparts. FIG. 7*c* has had filters 21 added, preferably for the elimination of leukocytes.

FIGS. 8 and 8*a* show the male connecting element 2 in accordance with the previously described design, to which a protective cap 22 is connected via the corresponding screw connection 23.

In a similar manner, the female connecting element 1, which also corresponds to the previously described design, is connected to a protective cap 24 in FIGS. 9 and 9*a*, The protective cap 24 corresponds in its shape to the male connecting element 1 The protective caps 23 and 24 have wingike protrusions, as illustrated in FIGS. 8 and 9, which simplify handling of the protective caps in releasing and tightening.

The protective caps 22 and 24 serve to protect the male connecting element 2 or female connecting element 1 and have threads 23 and 25 respectively in order to be reliably connected to the male or female connecting elements respectively so that a contact of the connecting elements to the environment is reliably prevented up to the release from the protective caps 22 and 24. The protective caps 22 and 24 further provide protection against externally arising forces or pressures arising internally in the line system Normally, the protective caps 22 and 24 are only removed directly before the assembly of the female and the male connecting elements by the operator.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A connection system for the connection of two or more sterile systems, comprising at least a male connecting element forming a closed end of a sterile, fluid-containing system and at least a female connecting element forming a closed end of a second sterile, fluid-containing system which can be aseptically connected to one another by inserting said male connecting element into said female connecting element, each of said connecting elements having a predetermined breaking point, said breaking points being aligned with one another when the two connecting elements are assembled so that they form a common predetermined breaking point enabling the closed ends of said connecting elements to be broken off together and fluid to flow through said connecting elements, said predetermined breaking point being located inside the fluid-containing system.

2. The connection system according to claim 1, wherein the two connecting elements can be connected to each other in a positively locking manner.

3. The connection system according to claim 1, wherein the connecting elements can be connected to each other by means of a screw thread.

4. The connection system according to claim 1, wherein the connecting elements can be connected to each other by means of a snap-in connection.

5. The connection system according to claim 1, wherein the connecting elements can be connected to each other by means of an adhesive connection.

6. The connection system according to claim 5, wherein the adhesive connection is a quick-hardening adhesive.

7. A connection system for the connection of two or more sterile systems, comprising at least a male connecting element forming a closed end of a sterile, fluid-containing system and at least a female connecting element forming a closed end of a second sterile, fluid-containing system which can be aseptically connected to one another, each of said connecting elements having a predetermined breaking point, said breaking points being arranged one above the other when the two connecting elements are assembled so that they form a common predetermined breaking point and can be broken off together, with the predetermined breaking point being located inside the fluid-containing system, and a disinfectant provided between contacting contact surfaces of the connecting elements.

8. The connection system according to claim 7, wherein the disinfectant has bonding properties.

9. The connection system according to claim 8, wherein the disinfectant is a quick-hardening adhesive.

10. A connection system for the connection of two or more sterile systems, comprising at least a male connecting element forming a closed end of a sterile, fluid-containing system and at least a female connecting element forming a closed end of a second sterile, fluid-containing system which can be aseptically connected to one another, each of said connecting elements having a predetermined breaking point, said breaking points being arranged one above the other when the two connecting elements are assembled so that they form a common predetermined breaking point and can be broken off together, with the predetermined breaking point being located inside the fluid-containing system, and cyanoacrylate being provided for connecting the two connecting elements.

11. The connection system according to claim 1, further comprising a protective cap having an external contour matched to the male connecting element.

12. The connection system according to claim 1, further comprising a protective cap in the form of a male connecting element that is connectable to the female connecting element for the protection thereof.

13. A connection system for the connection of two or more sterile systems, comprising at least a male connecting element forming a closed end of a first sterile, fluid-containing system and at least a female connecting element forming a closed end of a second sterile, fluid-containing system which can be aseptically connected to one another by inserting said male connecting element into said female connecting element such that said male and female connecting elements have an elongated nested portion with said closed portions adjacent one another, each of said connecting elements having a predetermined breaking point, said breaking points being adjacent one another in said elongated nested portion when the two connecting elements are assembled so that said breaking points align to form a common predetermined breaking point enabling the closed ends of said male and female connecting elements to be broken off together to open said connection system for fluid flow between said sterile systems, said predetermined breaking point being located inside the fluid-containing system so that said system remains sealed to an exterior thereof upon breakage of said connecting elements at said common breaking point.

14. The connection system according to claim 13 wherein said common breaking point is located approximately in a longitudinal middle of said nested portion.

15. The connection system according to claim 1, further including at least two bags and a tube system for the sterile transfer of fluid within a bag system.

16. The connection system according to claim 15 for the sterile transfer of biological or medical fluids in a bag system having at least two bags and a tube system.

17. The connection system according to claim 15 in a sterile blood bag system for the sterile transfer of blood or blood components.

18. The connection system according to claim 15 in a bag and tube system having at least one filter element for the sterile transfer of blood or blood components.

19. The connection system according to claim 15 in a bag system for the sterile transfer of infusion solutions or dialysis solutions.

20. The connection system according to claim 13 wherein said predetermined breaking points are formed by respective circular notches in said connecting elements.

21. The connection system according to claim 20 wherein said male connecting element has a notch on an inner surface thereof and said female connecting element has a notch on an outer surface thereof such that mating surfaces of said connecting elements when assembled in said nested portion are smooth.

* * * * *